(12) United States Patent
Kovács et al.

(10) Patent No.: US 7,888,085 B2
(45) Date of Patent: Feb. 15, 2011

(54) METHOD FOR INCREASED PRODUCTION OF BIOGAS

(75) Inventors: Kornél Kovács, Szeged (HU); Zoltán Bagi, Szeged (HU); Katalin Rákhelyné Perei, Szeged (HU); Gábor Rákhely, Szeged (HU)

(73) Assignee: University of Szeged, Szeged (HU)

( * ) Notice: Subject to any disclaimer, the term of this patent is extended or adjusted under 35 U.S.C. 154(b) by 769 days.

(21) Appl. No.: 11/720,130

(22) PCT Filed: Nov. 28, 2005

(86) PCT No.: PCT/HU2005/000125

§ 371 (c)(1),
(2), (4) Date: Nov. 7, 2007

(87) PCT Pub. No.: WO2006/056819

PCT Pub. Date: Jun. 1, 2006

(65) Prior Publication Data

US 2008/0124775 A1    May 29, 2008

(30) Foreign Application Priority Data

Nov. 26, 2004  (HU) .................................. 0402444

(51) Int. Cl.
| | |
|---|---|
| C12P 5/02 | (2006.01) |
| C12P 5/00 | (2006.01) |
| C12P 1/04 | (2006.01) |
| C12P 39/00 | (2006.01) |
| C12Q 1/02 | (2006.01) |
| A01C 3/00 | (2006.01) |
| C02F 11/04 | (2006.01) |
| C12Q 1/37 | (2006.01) |

(52) U.S. Cl. ...................... 435/167; 435/166; 435/170; 435/42; 435/29

(58) Field of Classification Search .................. 435/29, 435/42, 166, 167, 170
See application file for complete search history.

(56) References Cited

U.S. PATENT DOCUMENTS

| | | | |
|---|---|---|---|
| 3,383,309 A | 5/1968 | Chandler | |
| 5,529,692 A | 6/1996 | Kubler | |
| 5,651,890 A | 7/1997 | Trost | |
| 6,342,378 B1 | 1/2002 | Zhang et al. | |
| 6,569,332 B2 | 5/2003 | Ainsworth et al. | |

FOREIGN PATENT DOCUMENTS

| | | |
|---|---|---|
| EP | 0 263 796 A1 | 4/1988 |
| EP | 1 236 688 A1 | 9/2002 |
| HU | 195 978 | 11/1985 |

OTHER PUBLICATIONS

F.A. Rainey et al., 1994. Description of *Caldicellosiruptor saccharolyticus* gen. nov., sp. nov: An obligately anaerobic, extremely thermophilic, cellulolytic bacterium. FEMS Microbiology Letters, vol. 120, pp. 263-266.*
J. Sipma et al. 2004. Effect of carbon monoxide, hydrogen and sulfate on thermophilic (55%) hydrogenogenic carbon monoxide conversion in two anaerobic bioreactor sludges. Applied Microbiology and Biotechnology, vol. 64, pp. 421-428.*
Ueno, Y. et al., "Characterization of a Microorganism Isolated from Effluent of . . . ", Journal of Bioscience and Bioengineering, (2001) 397-400, 92(4).
Gössner et al., "*Thermicanus aegyptius* gen. nov., sp. nov., Isolated from Oxic Soil . . . ", Appl. and Envi. Microbiology (1999), 65, 5124-5133.
Goodwin, S. et al., "Influence of pH on Microbial Hydrogen Metabolism . . . ", Appl. and Environmental Microbiology, Feb. 1988 590-593, vol. 54, No. 2.
Sipma, J. et al., "Effect of carbon monoxide hydrogen and sulfate on thermophilic . . . ", Appl. Microbial.and Biotechnol., (2004) 64(3), 421-428.
Miyamoto, K. et al., "Chapter 4—Methane production" in "Renewable Biological systems . . . " (Series title: FAO Agricultural Services Bulletin—128) 1997, Osaka, Japan.
Nagamani, B. et al., "Biogas Production Technology: An Indian Perspective" Current Science, Jul. 10, 1999, vol. 77, Issue 1.

* cited by examiner

*Primary Examiner*—Jon P Weber
*Assistant Examiner*—Kailash C Srivastava
(74) *Attorney, Agent, or Firm*—Jason D. Voight (57) ABSTRACT

The invention relates to a method for increasing biogas production of thermophilic anaerobe systems. More closely, a biomass containing a consortium comprising polymer-degrading, acetogenic and methanogenic microorganisms is inoculated with a microorganism culture before the start of or during biogas production. Said microorganism is a thermophilic, acetogenic, hydrogen producing bacterium. As an example, *Caldicellulosiruptor saccharolyticus* is applied. According to the invention production if methane containing biogas is significantly increased.

The invention is useful for intensifying biogas production and thereby increasing its feasibility.

16 Claims, 7 Drawing Sheets

Use of Jerusalem artichoke as a substrate

Figure 9

Use of Jerusalem artichoke as a substrate

Figure 10

Sweet sorghum

METHOD FOR INCREASED PRODUCTION OF BIOGAS

This is the National Stage of International Application PCT/HU2005/000125, filed Nov. 28, 2005.

The invention relates to a method for increasing biogas production of thermophilic anaerobe systems wherein the biogas fermentation system is inoculated with a microorganism culture. The microorganism is selected to increase the production of an intermedier facilitating the process and/or expedite decomposition of the substrate, thereby promote microbial events resulting in biogas production. By the method of the invention the efficiency of plants presently working can be increased by a simple intervention, and the rate of return in case of new ones can be significantly decreased.

It has been known for long time that methane-rich biogas is formed when organic material from various sources is decomposed under anaerobic conditions. Numerous microbial strains participate in the process, these strains can be divided into three major groups. The first group include polymer-degrading bacteria; they hydrolyze large biomolecules and convert them into smaller molecules. These intermediates constitute the foodstuff for the acetogens, which produce organic acids, for example acetate, propionate, and butyrate. In certain cases the acetogens also produce hydrogen as a byproduct of their metabolism. The third group of microbes participating in biogas formation is called the group of methanogens. They act at the last step of the metabolic chain and generate the main components of biogas, i.e., methane and carbon dioxide. Thus, the microbes taking part in the degradation of organic material and in the generation of biogas depend on each others' metabolic activity: they form a consortium when functioning properly.

In anaerobic waste treatment technologies the utilization of the produced biogas (methane) decreases operational costs, which may make the treatment technology economically feasible in itself. The number of the economically competitive waste treatment facilities increases as the modern process management and engineering principles are widely implemented. These novel technologies more and more frequently utilize the concept of fermentative biogas production. Obviously, the gradual depletion of fossil energy sources increases the importance of using methane obtained from renewable resources to cover future energy needs. Therefore, intensive research and developmental work is going on worldwide in order to improve the energy production technologies from waste and biomass.

An important problem to be solved is the relatively low efficacy of the otherwise cheap and simple current one-fermenter systems.

It is well-known that methane formation from complex organic materials requires the participation of hydrolyzing, acetogenic and methanogenic microorganisms (see e.g. U.S. Pat. No. 5,529,692). Several attempts have been made to identify the rate limiting steps in the biogas production process and to determine the factors affecting biogas yield. According to U.S. Pat. No. 5,651,890, the rate limiting step generally can be found either in the polymer degradation phase or is the last, biogas formation phase, and the acetogenic phase consists of fast steps compared to the first and last phase.

According to the art several authors point out that the accumulation of a metabolic product generated by some of the microbes may easily inhibit the rate of the overall process. Furthermore, it has also been established that the optimum conditions for the individual bioconversion steps may vary. European Patent No. EP 1 236 688 goes as far as stating that the conditions required by the acetogenic and methanogenic microbes are incompatible. Therefore it is generally suggested that individual steps should be carried out advisably in separate reaction vessels or fermenters (U.S. Pat. Nos. 5,529,692 and 6,342,378) or al least in divided reaction spaces (Patent EP 0,262,796).

A specific difficulty identified in Patent EP 0 263 796 is the different optimal temperature requirement for the hydrolytic and acetogenic steps (above 37° C.) and for methanogenesis (below 37° C.).

According to U.S. Pat. No. 3,383,309 the rate of methanogenesis increased when hydrogen gas was introduced into the fermented waste water sludge. Other sources report on the inhibitory effect of hydrogen when it is administered from outside sources. The role of hydrogen in the biogas technology is thus ambiguous.

A team working at the Biological Research Center of the Hungarian Academy of Sciences and at the Department of Biotechnology of the University of Szeged has demonstrated earlier that, using communal solid household organic waste, waste water sludge or animal manure, the complex microbial process leading to biogas formation can be accelerated under mesophilic conditions if they interfere into the biogas production process according to their patented method of supplying microbial hydrogen for the methanogenic step [Kovács, K., C s. Bagyinka, I. Verebély, Process to increase the biogas production capability of mixed bacterium fermentation systems. Hungarian patent No. 195 978 (1985)]. The authors suggest that in mesophilic biogas production systems one of the rate limiting steps is the availability of hydrogen, which can be increased by adding hydrogen producing bacteria to the natural consortium. In the said Hungarian patent, however, it is not mentioned that the suggestion could be applied in thermophilic biogas production.

In spite of the long time that has passed since the original patent announcement and the extensive research and development work that has been done worldwide to improve the performance of the biogas production technologies, to the present inventors' knowledge, nobody has suggested that methane formation in thermophilic systems may be increased by the supply of in situ produced hydrogen using a hydrogen producer bacterium.

As the microbiological composition of the thermophilic biogas production consortia is completely different from the mesophilic counterpart, due to the huge difference in the operational temperature, conclusions based on findings for mesophilic systems can not extended to thermophilic biogas production. Therefore, our understanding of the mesophilic process cannot be extrapolated to the thermophilic technology.

J. Sipma et al. examined the effects of CO, hydrogen and sulfate ions on the thermophilic hydrogen and CO conversion at 55° C., under anaerobic conditions and using industrial waste waters and waste water sludge. They observed that depending on the environmental conditions and substrates, hydrogen and carbon dioxide were utilized by distinct microbes, e.g., methanogens, homo-acetogens, sulfate reducers [Sipma J at al., Appl. Microbiol. Biotechnol. 64(3) 421-428 (2004)].

It is also frequently cited in the scientific literature that thermophilic anaerobic systems are particularly vulnerable and are usually less stable from a microbiological point of view. Thus the metabolic equilibrium may shift significantly due to the accumulation of organic acids, and biogas production may stop. If this operational disaster takes place the fermenter has to be emptied and restarted using fresh organic substrate and the development of the proper microbial consortium usually takes a significant amount of time, sometimes even months.

In summary, we can conclude that there is still a need for efficient, economically feasible, and reliable thermophilic biogas production systems that may use various organic materials and wastes as substrate. It is of particular importance to have efficient, one-reactor systems in the thermophilic temperature range for the economically feasible biogas production.

The new process to be proposed is aimed to serve this goal by advising an environmentally friendly, efficient technology that allows large scale implementation.

The present inventors unexpectedly found that the efficacy of thermophilic biogas production technologies can be increased by adding a suitable hydrogen producing thermophilic microbial culture to the already existing natural biogas production consortium. The microbial activity of methane producers can be augmented this way in the thermophilic consortium, by supplying sufficient reducing power and substrate for biological methane production. An additional advantage can be employed if we use a hydrogen producer strain that contributes to the better utilization of the organic substrate, e.g., by its capability to hydrolyze biopolymers.

According to the technology of the invention the anaerobic biogas production can be intensified via a relatively simple biotechnological method. This improves the economical feasibility of the overall system when wastes and side products generated in food processing and agricultural activities are converted to biogas in an anaerobic treatment technology.

The efficiency of biogas production using our method is significantly improved and exceeds the efficacy of similar mesophilic processes. Unexpectedly the thermophilic system proved to be useful in a wide variety of applications using biomass from many sources. This indicates that the various thermophilic microbial consortia are similar in at least one aspect, i.e., in situ hydrogen production is a crucially important beneficial step in all thermophilic systems investigated so far.

We found that *Caldicellulosiruptor saccharolyticus* is a particularly suitable microorganism to bring about the desired advantageous effect.

BRIEF DESCRIPTION OF THE INVENTION

According to an aspect the invention relates to a method for producing biogas under anaerobic conditions by fermenting biomass, using a consortium comprising a methanogenic microorganism, comprising the steps of
starting the fermentation of the biomass and forming, from the microorganisms participating in the fermentation, a consortium capable of producing biogas under thermophilic conditions, wherein said consortium comprises at least polymer degrading and methanogenic microorganisms,
inoculating the biogas producing system by a culture of hydrogen producer, thermophilic microorganism,
fermenting the biomass under conditions wherein the microorganisms are active,
collecting the produced biogas.

According to a further aspect the invention relates to a method for increasing biogas production by fermenting biomass under anaerobic and thermophilic conditions, by using a consortium comprising a methanogenic microorganism, wherein before starting biogas production or during biogas production a culture of thermophilic, hydrogen producing microorganism is added, at least once, to the biogas producing consortium. Preferably, the consortium further comprises a polymer degrading microorganism and/or before the start of biogas production or during biogas production a polymer degrading microorganism is added, at least once, to the consortium.

Upon fermentation thermophilic conditions are provided, preferably the temperature is set to 45-70° C., more preferably to 50-60° C.

Upon fermentation, if needed, the pH is set. Preferably, at the beginning of the fermentation the pH is between pH 6 and pH 8 more preferably between pH 6.5 and pH 7.5, highly preferably between pH 6.5 and pH 7, between pH 6.8 and pH 7.2, e.g. about pH 7, or between pH 7 and pH 7.5.

Preferably, the microorganisms of the invention are bacteria. According to the invention the microorganisms are thermophiles, i.e. are capable of exerting their desired effect under thermophilic conditions, i.e. temperature range. Preferably, the temperature under the thermophilic conditions used in the invention is preferably 40-90° C., more preferably 45-70° C., highly preferably 50-60° C.

The hydrogen producing bacterium used according to the invention is preferably an acetogenic bacterium.

Thus, according to the invention an acetogenic bacterium is used which is capable of working under thermophilic and anaerobic condition, and which is a hydrogen producer.

According to a preferred embodiment the bacterium used in the invention has a polymer degrading, preferably a carbohydrate (polysaccharide) degrading activity.

According to a further preferred embodiment of the method of the invention additives can be used. The additives may be e.g. nutrients or foodstuffs for the microorganisms or bacteria, e.g. various organic compounds or mixture thereof. Certain compounds, e.g. sugar may result in a substrate inhibition; therefore, experiments should be carried out to determine the useful quantity.

Materials of large surface area, e.g. wood chips, can be applied as well, and in preferred embodiments the cells can be bound to carriers (immobilized to), e.g. rhyolitic tuff.

Preferably, the biomass can be
liquid manure, e.g. pig slurry or manure of poultry
waste water sludge, e.g. lipid rich (fat) waste water sludge,
plant waste, e.g. straw, maize (corn) stalk, corn cob, etc, preferably plant waste from high energy plants, e.g. bagasse or sorghum, artichoke, e.g. Jerusalem artichoke, barley, potato, wheat, sugar-beet, oat, rape etc.
or any mixture thereof.

According to a further preferred embodiment sedimented or pelleted (e.g. by centrifuge) cells are used, or immobilized cells (e.g. cells immobilized to e.g. rhyolitic tuff or perlite) are used

BRIEF DESCRIPTION OF THE FIGURES

Intensified biogas production from pig slurry (FIG. 5), lipid-rich waste water sludge (FIG. 6) and the mixture of the two substrates (FIG. 7). The values represent the methane content (%) compared to the 14th day value.

DEFINITIONS

Some of the terms used herein are explained below; the rest of the terms and expressions are used as common in the technical language of the pertinent field of art.

"Biomass" means the organic material of living or non-living organisms (i.e., of microbial, plant or animal origin) and the byproducts of any industrial processing that use these materials as well as the organic fraction of biological origin produced in agricultural activities and human communes. The biomass or its fraction can be converted using fermentation.

A "microbial consortium" means a population of several microbial species, involving at least two independent strains or species, where at least one metabolic product of one species is utilized by an other one, i.e. the microorganisms cooperate or act together.

"Thermophilic conditions" mean an environment that is suitable for microbial growth and has a minimum temperature of 40° C., preferably of 45° C., and more preferably of 45-75° C. or at least 50° C., highly preferably or 50-60° C.

An "acetogenic bacterium" is a microbe that produces small organic acids as one of the end products of its fermentation, e.g., acetate, propionate, or butyrate, from the degradation products of biopolymers such as polysaccharides or proteins.

A "hydrogen producing" acetogenic bacterium is capable of converting substrate molecules of biopolymer origin (e.g. polysaccharides, proteins) to hydrogen gas.

The acetogenic and hydrogen producing acetogenic bacteria to be used in the patented process act preferably but not exclusively as part of a microbial consortium.

DETAILED DESCRIPTION OF THE INVENTION

The invention is described below in a more detailed manner, partly by way of examples. The examples are of merely exemplary nature, and they are not to be construed as delimiting the claimed scope.

The relates to a method for increasing biogas production. In principle, the method can be applied in biogas producing systems utilizing any kind of organic substrates.

An essential element of the method of the invention is the inoculation of the biogas producing system by an appropriate microorganism culture, wherein said biogas producing system operates at thermophilic temperatures by anaerobe fermentation.

The inoculation can be used both during the start-up period of a biogas fermenter and during the operational period of an already established biogas fermenting system.

The following considerations should be taken into account when the added microorganism is selected: the microbe should be a hydrogen producing, thermophilic (growing at 45-70° C. preferentially between 50-60° C.), anaerobic microorganism. Preferably, it should be an acetogenic bacterium.

The biological activity of the selected microorganism should facilitate the microbiological events leading to biogas production, e.g., through the generation of intermediers suitable for increased biogas yield or through a more thorough fermentation of the original organic substrate. Highly, preferably, the microorganism fulfils both of these requirements.

The appropriate bacterium may be selected by e.g. the following approach:

Among thermophilic, acetogenic microorganisms known in the art a strain having hydrogen production capability is selected. The hydrogen production capacity of the strain can be tested by any know method [e.g., Goodwin S. at al., Appl. and Environmental Microbiology, 590-593, February (1988), Strocchi A and Levitt D L, The Journal of Clinical Investigation, 89 1304-1311 (1992)]

According to an other strategy any newly isolated thermophilic, polymer degrading strain can be tested. In this case the polymer degrading capability is demonstrated by growing the bacteria on the particular polymer (oligo or polysaccharides) as a sole carbon source. Those that can grow on the particular carbon source will be capable of its metabolism. Tests should be carried out under anaerobic (anoxic), thermophilic conditions, at nearly neutral pH. If the selected microbe can grow in a biogas forming consortium, it may contribute to the intensification of biogas production.

It is advisable to search among acetogenic bacteria as they have a good chance to become a member of the natural consortium, which is a prerequisite of the increased biogas production.

The hydrogen evolving activity of the isolated strain should be checked.

According to a preferred method the selected or isolated strain is tested for its polymer degrading activity. This can be e.g. the degradation of proteins and/or polysaccharides.

These tests can be performed using routine methods by adding the substrate to the bacterium culture under anaerobic and thermophilic conditions. The system should advisably lack other carbon sources.

According to a further, preferred approach one may screen the known thermophilic, polymer degrading, protein degrading or carbohydrate degrading microorganisms for an acetogenic bacterium strain of increased hydrogen producing activity.

Although the strain(s) selected according the above-mentioned procedures will most likely be suitable to be used in the invention, model experiments are advisably needed before large scale application to see if the selected strain can indeed fit into the thermophilic biogas producing consortium.

In these laboratory scale experiments the selected strain(s) are tested for their ability to adapt to the thermophilic consortium. Biogas production is modeled such a way that before the start of the fermentation or during the developed process the separately cultivated bacteria are added and biogas production is monitored together. The control experiment is identical in every aspect except that the intensifying bacterium is not added to the system.

The results will demonstrate the increased biogas production rate and/or absolute amount and will tell if the methane content of the biogas is acceptable.

In addition to the volumetric measurement of the produced biogas, its composition is determined. One can use any of the widely known and accepted techniques for this purpose, e.g., element analysis, mass spectrometry, spectroscopic methods, gas chromatography etc.

Based on prior information it is assumed that good and suitable intensifying microorganisms is likely to be found among the following species:

*Thermotoga* genus, for example *Thermotoga elfii, Thermotoga maritima, Thermotoga neopolitana,*

*Thermococcus* genus, for example *Thermococcus litoralis, Thermococcus sibiricus, Thermococcus celer, Thermococcus pacificus*

*Pyrococcus* genus, for example *Pyrococcus woesei, Pyrococcus furiosus,*

*Clostridium* genus, for example *Clostridium thermocellum, Clostridium butyricum*

*Ruminococcus* genus, for example *Ruminococcus albus*, or according to a preferred embodiment the *Caldicellulosiruptor* genus, more preferably *Caldicellulosiruptor saccharolyticus*. According to a highly preferred embodiment the microorganism is the *Caldicellulosiruptor saccharolyticus* DSM 8903 (DSMZ, German Collection of Microorganisms and Cell Cultures, Mascheroder Weg 1b 38124 Braunschweig GERMANY).

A few additional examples of potential candidate bacteria to be used in the realization of the patented technology are as follows:

*Caloramator fervidus*, for example strain ATCC 43204, deposited as *Clostridium fervidus* [Patel B. K. et al J. Bacteriol. 37, 123-126 (1984)],

*Coprothermobacter proteolyticus*, for example strain ATCC 35245, deposited as *Thermobacteriodes proteolyticus* [Ollivier et al Int. J Syst. Bacteriol. 35 425-428 (1985)],

*Thermoanerobacterium thermosaccharolyticum*, for example strain *T. thermosaccharolyticum* KU110 [Ueno Y et al., Journal of Bioscience and Bioengineering, 92(4) 397-400 (2001)],

*Thermotoga neapolitana* [van Ooteghem S. A. et al., Appl. Biochem. Biotechnol *Spring* 98-100 177-89 (2002)],

*Moorella thermoacetica* [Gner et al., Appl. Envi. Microbiol 65 5124-5133 (1999)].

A preferred example as inoculum is *Caldicellulosiruptor saccharolyticus* and preferably the strain DSM 8903. This strain and other strains possessing similar properties can be used for the intensification of biogas production. The size of the inoculum is usually 5-10% of the total fermenter volume if a growing culture is used.

In practice the method of the invention can be carried out as follows:

A growing bacterial culture is produced using the appropriate medium, at 40-70° C.

The biomass substrate is filled into the fermenter and biogas production is started using any of the known procedures and a biogas production system using natural consortia of microorganisms is developed. The biogas producing fermenter is inoculated with the cultivated monoculture of the selected bacterium, e.g., *Caldicellulosiruptor saccharolyticus*. If necessary the inoculation is repeated as the fermentation progresses.

At the start-up phase of the biogas process a minimum requirement is to maintain the system at the appropriate temperature and under anaerobic conditions. The anaerobic degradation of most biomass sources develops spontaneously although the start-up phase may need considerable time in certain cases. The appropriate pH, which is usually near neutral, should be maintained when some biomass sources are fermented, e.g., biomass of plant origin; in other cases (e.g., waste water sludge, animal manure) the pH becomes stable without adding any buffering substance.

The start-up phase can be shortened by using inocula for example from an anaerobic waste water sludge treatment facility. Inocula can be obtained from any thermophilic anaerobic digester or can be prepared separately by using animal manure or waste water sludge and incubating it under anaerobic conditions at thermophilic temperature and incubating it until fermentation starts.

One can also use inoculum from a mesophilic digester, but in this case the microbial consortium should be adapted to thermophilic temperature, by slowly elevating the temperature.

The preferred experimental vessel is a single space anaerobic fermenter capable of continuous or semi-continuous operational modes.

About 10-20% of the digested (fermented) biomass is replaced continuously or at specified and regular time intervals by adding fresh biomass to the system through a closed, anaerobic system.

The biogas produced is transferred from time to time or, preferably, continuously and used for energy production. Biogas can be utilized near the site of its production.

It is a common observation that the larger the fermenter volume the slower is the start-up phase, however, the system reaches a stable operational performance after some time in all cases tested.

In order to facilitate the economically feasible and continuous large scale production of the selected intensifying microorganism(s), a novel and simplified fermentation technology has been developed and is being practiced at the fermentation facility of Corax-Bioner Inc. The facility has a total working volume of 80 $m^3$.

EXAMPLES

Example 1

Selection and Testing of the Suitable Hydrogen Producing Bacterium

We have selected an anaerobic acetogenic bacterium that grows well between 45-70° C. and preferably at 50-60° C.

The hydrogen evolving activity of the selected strain(s) can be tested using the following method:

A direct method to measure hydrogen evolving activity uses gas chromatography. The bacteria are cultivated in a sealed 50-150 ml glass vessel in its preferred culture medium under anaerobic conditions. When the optical density of the culture reaches at least 0.4/cm at 600 nm, a gas sample is removed anaerobically from the head space of the vessel and injected into the gas chromatograph directly. The hydrogen peak, which is identified by using a gas mixture of known composition, indicates the hydrogen evolving activity of the bacterium.

It is customary to screen several, independently cultivated bacterial stains and apply in the method of the invention the one displaying the highest hydrogen producing activity.

Testing the Polymer Degradation Capability of the Hydrogen Producer Strain

According to a preferred method strains degrading polysaccharides are screened. An example of how this can be tested is the following:

The reagent used to test polysaccharide degrading activity is dinitrosalycilyc acid. The polysaccharide is mixed with water and a known amount of the supernatant of the precultivated bacteria is added. pH is adjusted to 4.8 using citrate buffer. After an incubation period of usually 30 min at 50° C. the reaction is terminated by adding dinitrosalycilyc acid. The optical absorbance is determined at 550 nm. If the measured value exceeds that of the control sample, the bacterium produces extracellular polysaccharide degrading enzyme(s).

Protein degradation activity is also determined by using a spectrophotometer. The supernatant of the precultivated bacterium strain is added to the protein sample and the pH is adjusted to 7.0 with phosphate buffer. Absorbance of the sample is measured at 280 nm. A decrease in absorbance indicates protein degradation activity.

Maintenance and Cultivation of Bacteria

The following two strains were used in the following experiments:

Mesophilic hydrogen producer: *Enterobacter cloacae* DSM 3264 [DSMZ—Deutsche Sammlung von Mikroorganismen und Zellkulturen GmbH (German Collection of Microorganisms and Cell Cultures), Mascheroder Weg 1b 38124 Braunschweig GERMANY, http://www.dsmz.de/strains/no003264.htm]; Gram(−), which can grow both aerobically and anaerobically between 20-40° C.

Thermophilic Hydrogen Producer: *Caldicellulosiruptor saccharolyticus* DSM 8903 [DSMZ—Deutsche Sammlung von Mikroorganismen und Zellkulturen GmbH (German Collection of Microorganisms and Cell Cultures), Mascheroder Weg 1b 38124 Braunschweig GERMANY, http://www.dsmz.de/strains/no008903.htm]: Gram(+), anaerobic bacterium cultivated between 40 and 80° C.

Maintenance of the strains were carried out according to the instructions of the supplier.

Both strains were stored in a frozen state at −70° C., they were cultivated in the specified respective DSM media, i.e., DSM-1 for *Enterobacter* and DSM 640 for *Caldicellulosiruptor*. Inocula were routinely cultivated in 150 ml sterile glass vessels under oxygen free nitrogen gas to ensure the anaerobic environment.

Growth was followed by optical density measurement due to light scattering in a GENESYS6 spectrophotometer.

Example 2

Preliminary Experiment to Produce Biogas from Pig Slurry

Pig slurry was used in this preliminary experiment. The slurry substrate was dispensed in 50 ml aliquots into glass vessels of 100 ml volume and sealed air tight. Some of the vessels were inoculated with 5 ml of pure culture of *Caldicellulosiruptor saccharolyticus*. The headspace was replaced with nitrogen gas. Incubation was carried out at 55° C. A gas sample was removed anaerobically from the head space every day and the gas was subjected to qualitative and quantitative analysis. The results are presented in FIG. 1.

Figure 1:
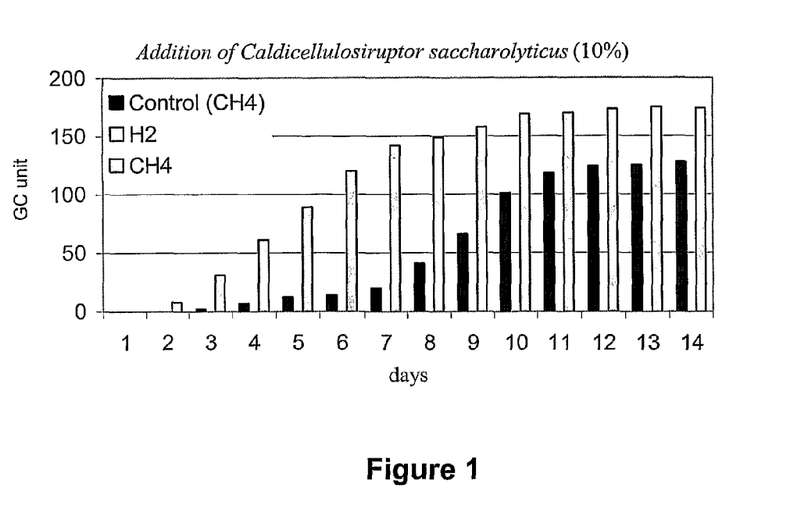
FIG. 1 shows the anaerobic methane production in GC units from pig slurry when the system is inoculated with a pure culture of *Caldicellulosiruptor saccharolyticus*.

The x axis of the graph indicates days after the start of the experiment, the y axis shows the amount of the biogas in GC units. When compared to the control samples, the inoculated ones clearly display that methane production starts faster and the overall biogas generation produces more gas than in the controls.

This example illustrates that biogas production rate is increased and the produced volume of biogas also increases upon the addition of the selected hydrogen producer strain.

Anaerobic Degradation of Pig Manure and Selected Additives

Figure 2:
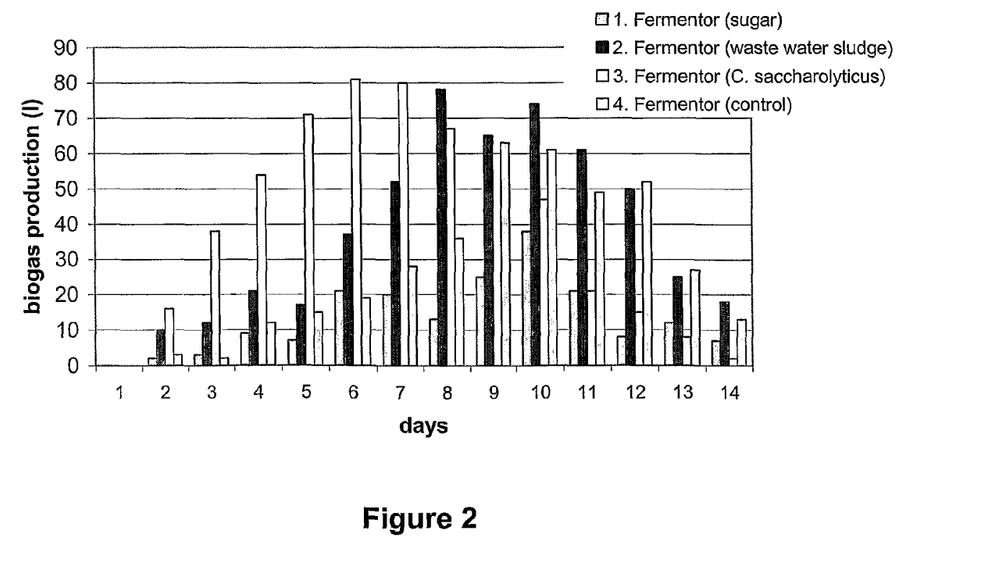
FIG. 2 shows the biogas production from pig slurry and various additives. The added biomass sources were waste water sludge, sugar (saccharose) and wood bark.

In the next example the basic substrate for biogas production was pig slurry again, but it is treated in 50 liter fermenters and additives were tested for their ability to augment biogas production. The additives examined were waste water sludge, sugar (saccharose) and wood chips. Waste water activated sludge contains mostly microorganisms and some undigested organic material, sugar is a preferred carbon source for most microbes and wood chip increased the surface available for the microbes. FIG. 2 demonstrates that in the presence of *Caldicellulosiruptor saccharolyticus* biogas production started very quickly and the overall gas production volume clearly exceeds that of the control. When sugar was added to the system, substrate inhibition was observed.

This example provides additional evidence for the intensified biogas production when the process is scaled up and demonstrates that certain additives are beneficial for the biogas production.

Example 3

Biogas from Bagasse

Figure 3:
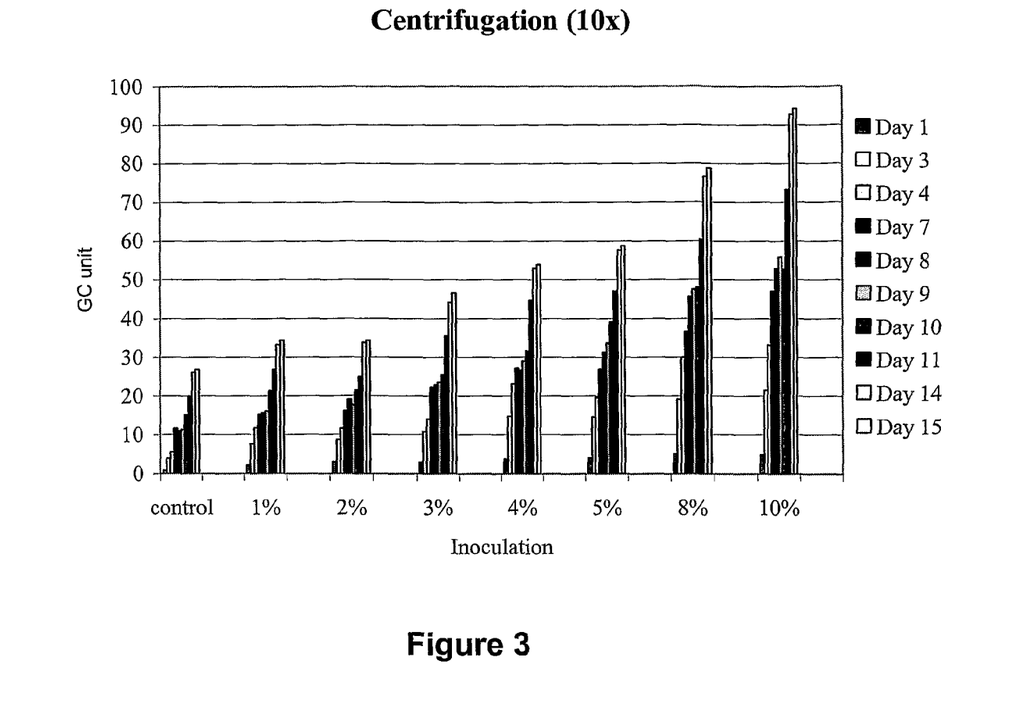
FIGS. 3 and 4 demonstrate biogas production from bagasse. Pure culture of *Caldicellulosiruptor saccharolyticus* was added in various amounts and the intensification effects of the pelleted bacteria (FIG. 3) and of the same bacteria immobilized on perlite (FIG. 4) were compared.
Figure 4:
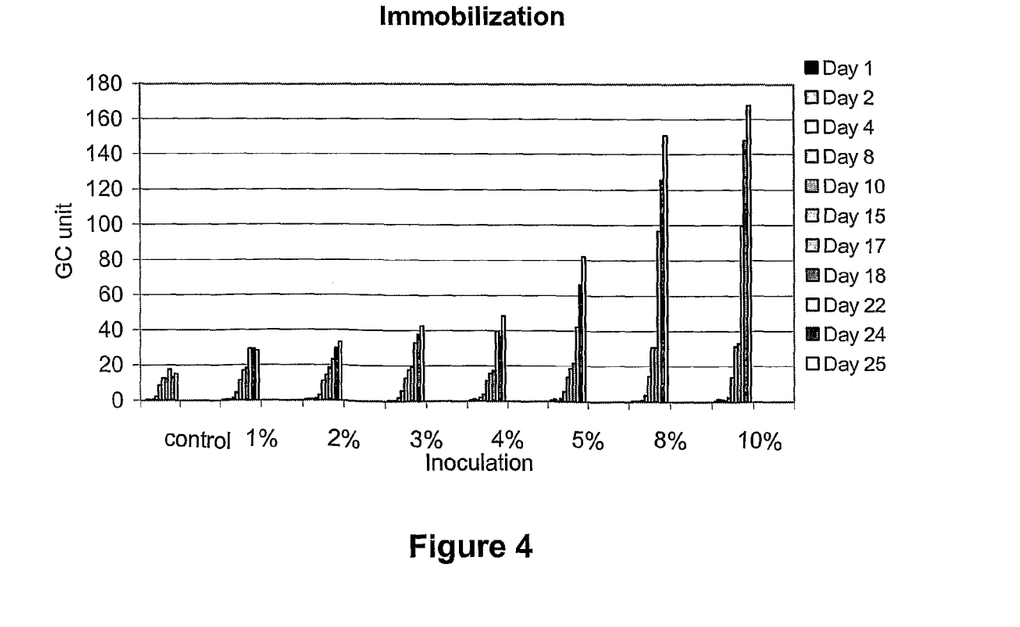

The dried biomass was used at various concentrations, in 1-10 V/V % range. The tests were carried out in sealed glass vessels of 100 ml volume. The experiments aimed to determine the intensification conditions using centrifuged bacteria (FIG. 3) and the same bacteria immobilized on rhyolitic tuff (perlite) (FIG. 4).

The example demonstrates that biogas production can be intensified even when the substrate is predominantly a low biogas yield, cellulose rich material, i.e. an energy grass. It has also been concluded that concentration of the bacteria by centrifugation and even more advantageously through immobilization on a cheap mineral carrier material may further improve biogas production. Several high specific surface carrier material can be used for immobilization of the hydrogen producing bacteria; perlite, a low cost and abundant material, is just one of them.

Example 4

Studying Methane Production By Degrading Pig Slurry

In this example, as a first experiment, biogas formation from pig slurry was investigated. The goal of the experiment was to determine the amount of biogas produced from this substrate. These data obtained here were used as control values in the subsequent experiments, to compare results obtained later.

Figure 5:
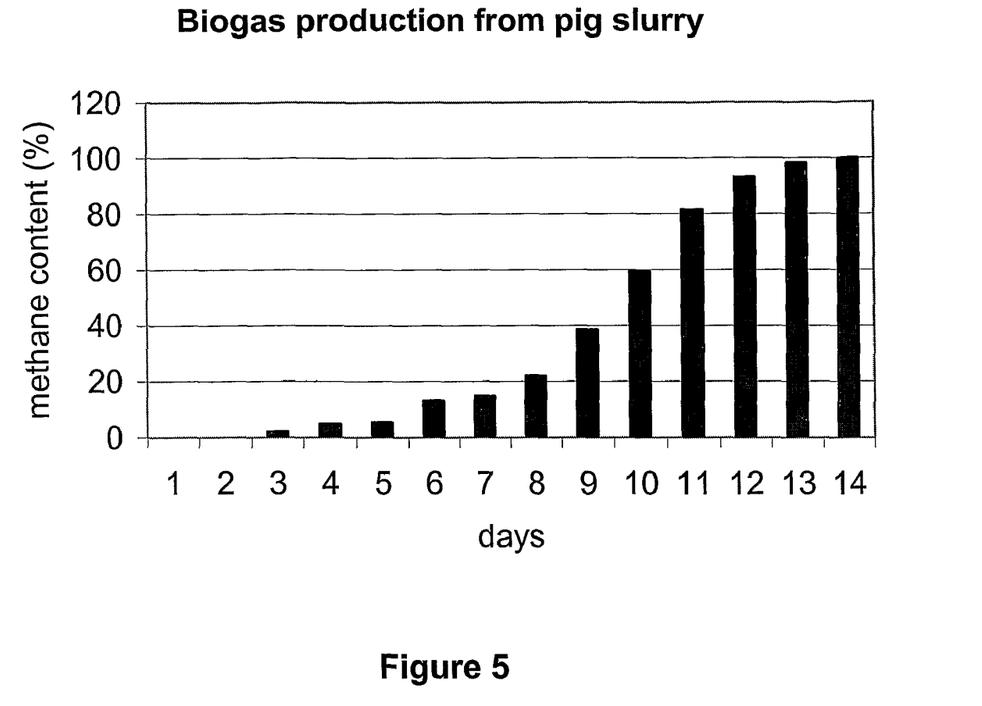

FIG. 5 shows the daily methane production, measured at taking aliquot samples. The numbers indicate the cumulative biogas production measured in the head space of the glass vessels. The value obtained on the $14^{th}$ day was considered 100% for comparisons. As seen on the figure, methane production starts on the $7^{th}$ or $8^{th}$ day. The vessels were incubated at 55° C., which was significantly higher than the initial temperature of the biomass. It is conceivable that the microbes present in the slurry had to adopt themselves to the thermophilic conditions and it took time to develop a stable thermophilic consortium. This explains why biogas production started only after an extended period of time (day 7 or 8); actually by this time methanogens, initiating an intensive methane production, were grown up.

In the next experiment lipid rich waste water sludge of a slaughter-house was examined. The experimental conditions were identical to those described above, i.e., 50 ml of substrate dispensed into 150 ml vessels and anaerobic incubation took place at 55° C. in a thermostated chamber.

Figure 6:
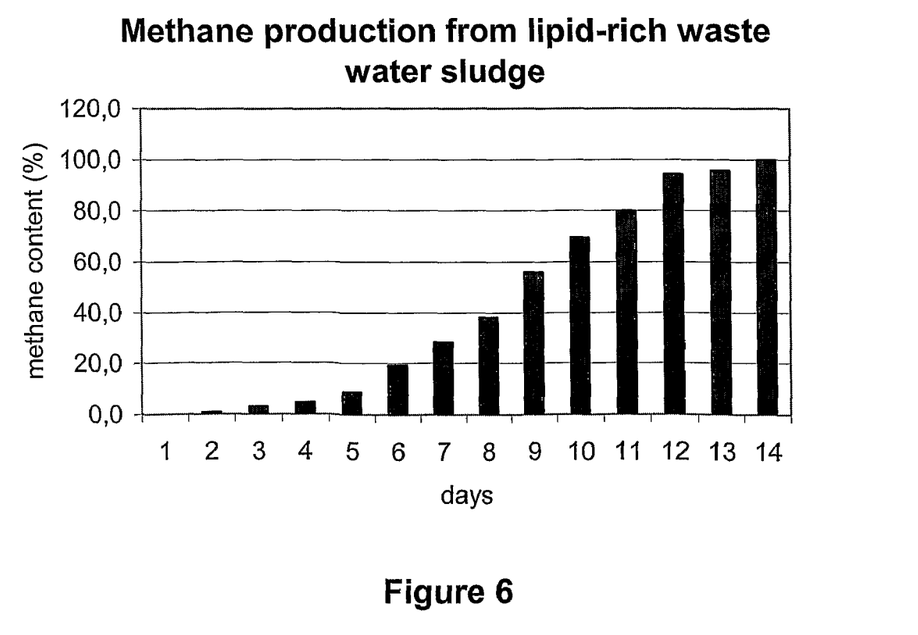

FIG. 6 shows the volume of accumulated biogas in the vessels, day by day. The experiment was terminated on day 14 and the total amount generated by this time was considered as 100%. Intensive methane formation was observed from day 5 or 6 and biogas production decreased after day 12. The experiment demonstrated that waste water sludge is a suitable substrate for biogas production.

Figure 7:
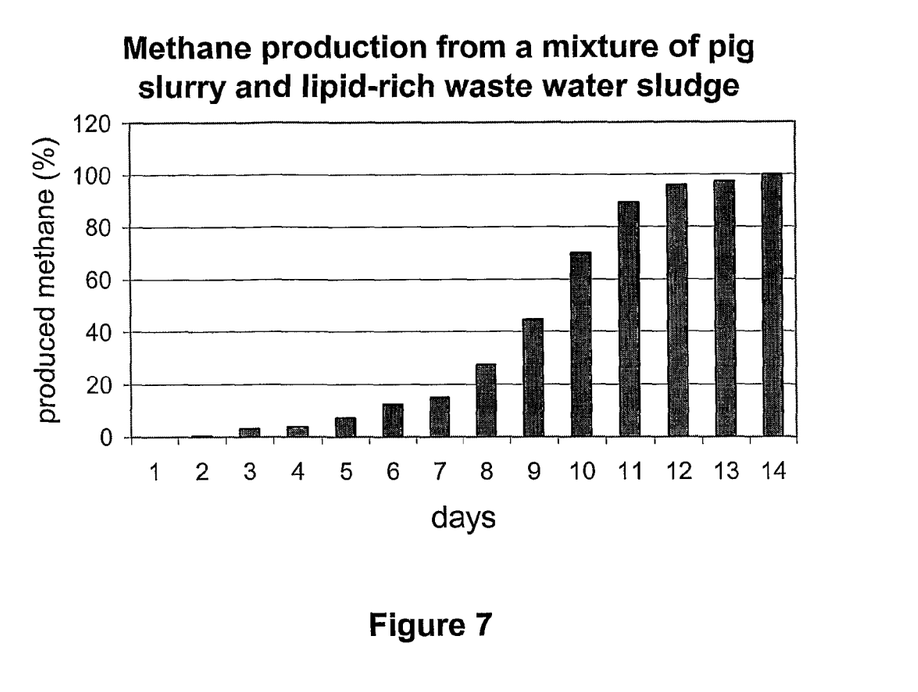

In the next experiment, a 1:1 (by volume) mixture of pig slurry and the same waste water sludge was tested. FIG. 7 presents the data, which demonstrate that, similarly to the results described above, the onset of biogas production happened after a few days and intensity of production is decreased after day 12.

Figure 8:
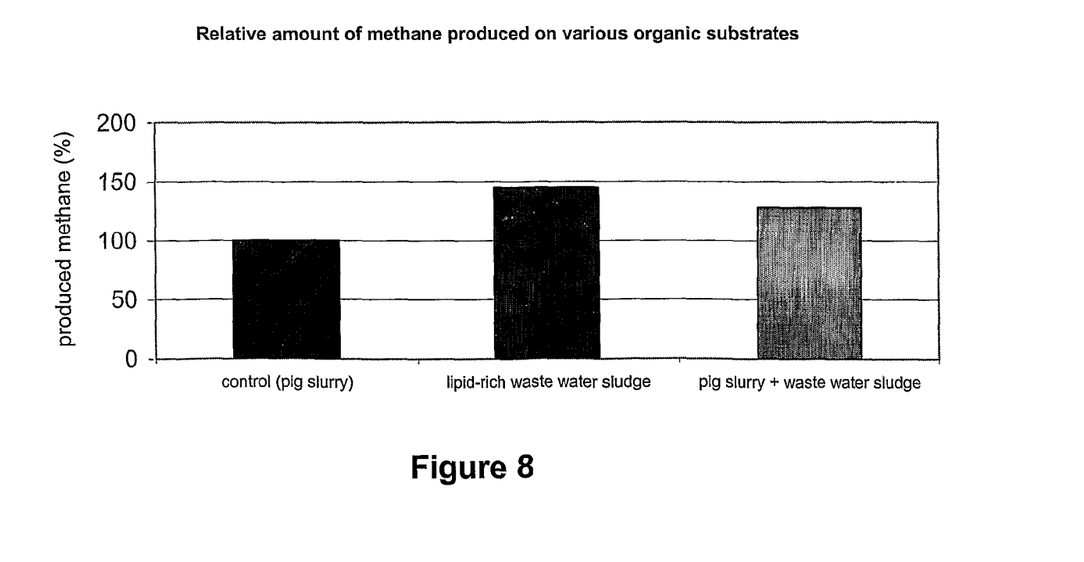
FIG. 8 summarizes the total methane production in the individual experiments for comparative purpose.

FIG. 8 shows the comparison of the cumulative biogas productions using these various substrates.

The main conclusions of these experiments are:
lipid rich waste water sludge is suitable for biogas production, and
using this substance is added, by an approximately 45% more biogas could be produced as compared to pig slurry alone.

It is recognized that the higher digestible organic content in the lipid rich waste water sludge is responsible for the elevated biogas productivity.

When a mixture of the two substrates was employed the increase of biogas production was only 28%, which is below the value obtained using the sludge alone. The organic solid content of the pig slurry used in these experiments was lower than that of the sludge, thus the dilution effect may explain the lower performance of the pig manure and its mix with the sludge.

Example 5

Various Biomass Substrates of Plant Origin

Figure 9:
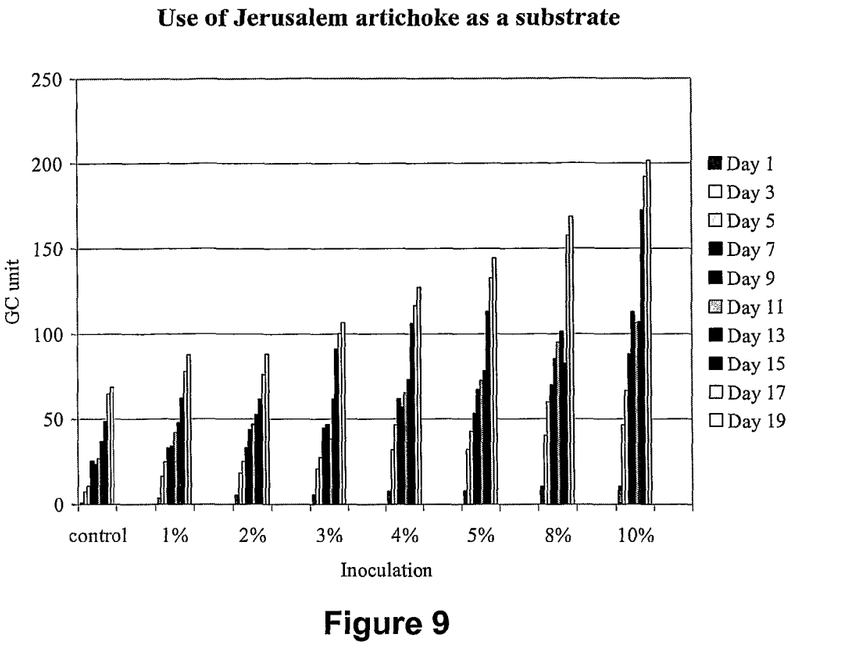
FIGS. 9 and 10 show intensified biogas production (in GC units) using Jerusalem artichoke as biomass source. Varying amounts of *Caldicellulosiruptor saccharolyticus* pure cultures were added to the inoculated samples. In the experiment demonstrated on FIG. 9 the bacterium cells are used together with the medium, whereas on FIG. 10 the effect of pelleted cells is shown.
Figure 10:
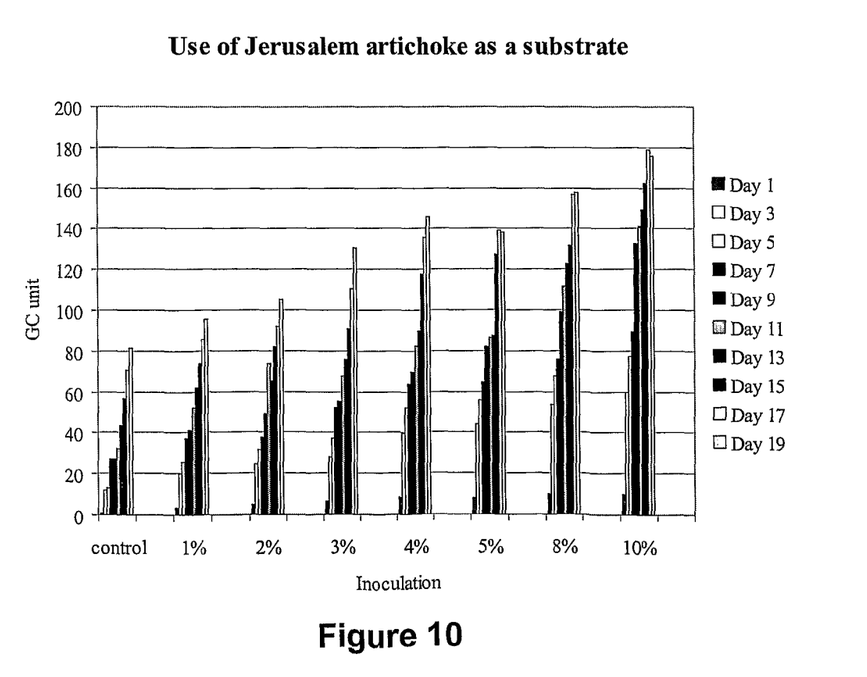

In addition to bagasse, other plant biomass substrates have also been tested for the applicability of the biotechnological intensification of biogas production. The next experiment investigated the use of Jerusalem artichoke as energy plant and aimed to test if the beneficial effect of the presence of *Caldicellulusiruptor saccharoyticus* could be observed. The bulb of Jerusalem artichoke, which contains most of the stored sugars and is found in the roots was chopped up first. FIG. 9 shows the results when the biomass was treated with the growing bacterial culture (i.e., a small fraction of the growth medium was also added into the reaction mixture) and FIG. 10 presents similar data obtained with centrifuged cells.

The main conclusion from this experiment is that Jerusalem artichoke is a particularly suitable source of biomass for biogas production. This plant can be cultivated using cheap technology and produces high concentration of biomass. It is also concluded that the process described here can be useful with other energy plants as well.

In Examples 3-5 we have demonstrated that biogas production can be intensified as a result of the addition of a suitably selected bacterium (which was *C. saccharolyticus* in these examples but it could be an other strain as well), and there is a direct cause-effect relationship accompanying the addition of the bacteria in various forms.

Example 6

Comparison of Mesophilic and Thermophilic Systems Utilizing Various Substrates

The experiments to be reported below were based on the results obtained during the previous phase of the developmental work and served to compare the biogas productivity of mesophilic and thermophilic systems.

The substrates were used in 10-15 g quantity and the dry matter content was precisely determined. Then a suspension was prepared by the addition of water or buffer solution. The reaction volume was standardized so that each gram of dry matter was dispersed in 40 ml of water or aqueous solution, and the volume of the substrate was augmented accordingly. The final volume was thus around 400 ml in each experiment. When substrates of plant origin were studied, it was suspended routinely in phosphate buffer (pH7).

Sealable glass vessels of 500 ml volume were used, immediately after filling in the substrate the vessels were sealed air-tight and the headspace was made anaerobic by flushing it with high purity nitrogen gas. The reaction vessels were connected to containers filled with saturated salt solution and the volume of the produced biogas was determined by measuring the amount of salt solution displaced by the biogas.

The measured values were normalized to the gas volume at 30° C. in order to make sure that the data do not contain systematic error due to the temperature dependence of gas expansion. The productivity values are expressed as biogas ml per 1 g of organic solid for direct comparison.

The gas composition of biogas (e.g. methane and carbondioxide) was followed using a gas chromatograph (SRI 8610C) fitted with a PorapackQ column and thermal conductivity detector. The gas chromatograph was calibrated using standard methods and gas mixtures.

The methane content of the biogas ranged between 50-60% in the experiments. Figures show the total biogas production.

The hydrogen producing bacteria were separately cultivated as described in Example 1 and the fresh cultures were added to the vessels in 5-20 v/v % (preferably in 10 v/v %) concentration.

As specified above, *Enterobacter cloacae* DSM 3264 was used as mesophilic hydrogen producer at 30° C. and *Caldicellulosiruptor saccharolyticus* DSM 8903 was employed as thermophilic hydrogen producer at 55° C.

Controls were supplemented with equal volume of fresh media, without bacteria.

Biogas formation was measured daily and plotted as seen in the figures. The cumulative biogas production was estimated after normalizing the gas volumes and adding up the partial values. The total generated biogas (normalized for 1 g organic solid and for 30° C. temperature) was compared with the same numbers obtained with the controls and their ratio was defined as the degree of intensification.

Figure 11A:
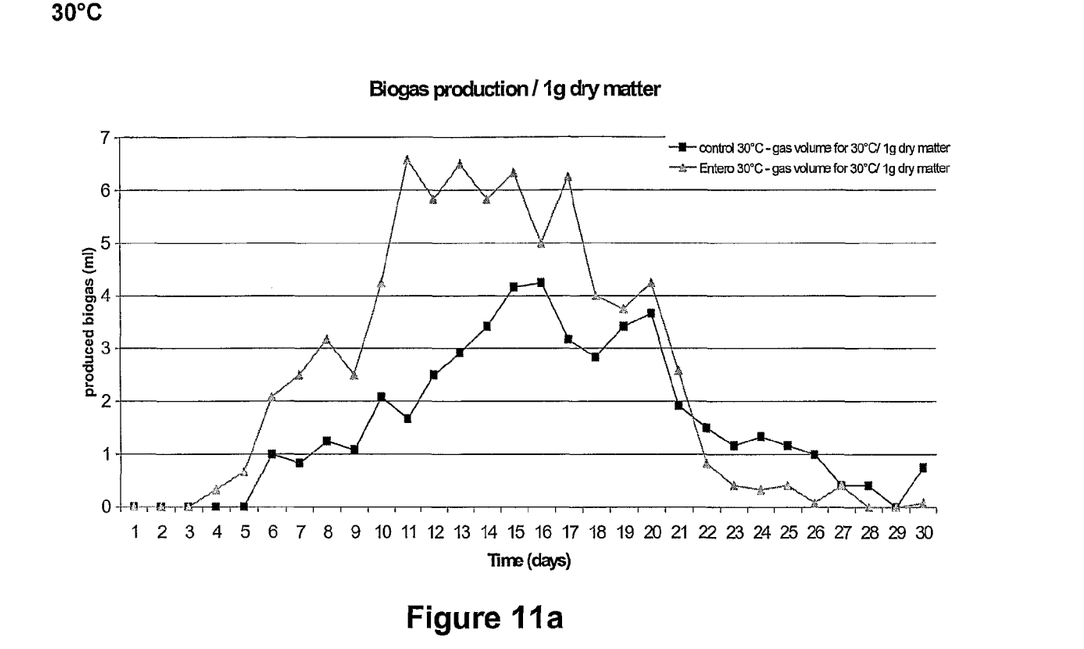
FIGS. 11a and 11b presents the intensified and control biogas production data using sweet sorghum as substrate under mesophilic (11.a.) and thermophilic (11.b) conditions. The biogas production is expressed in volumes normalized to the gas volumes at 30° C. and to unit dry material content of the substrate.
Figure 11B:
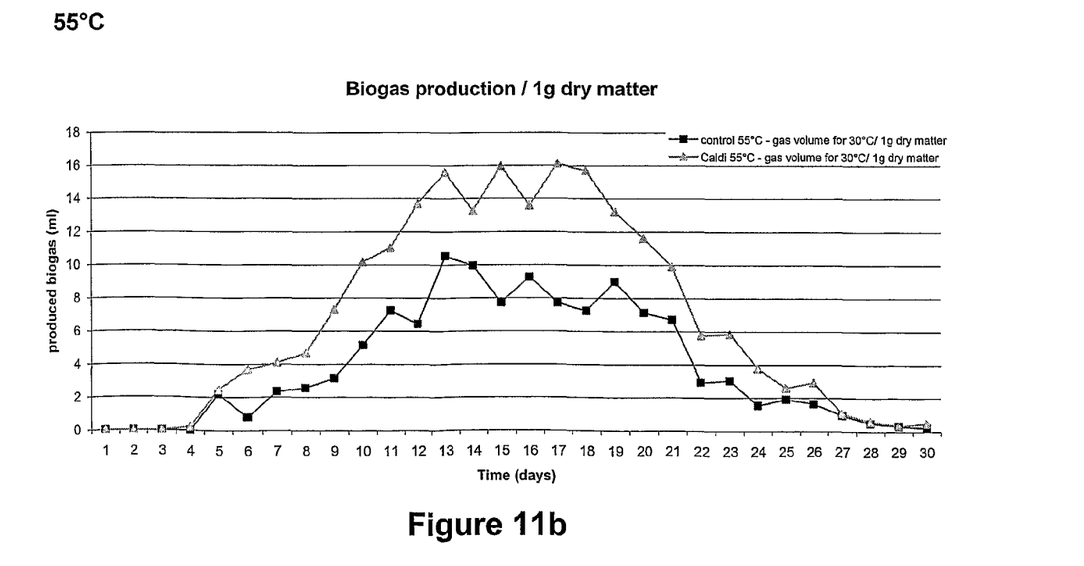

The data are presented in FIGS. 11a and 11b for sweet sorghum and the corresponding data are summarized in tables below for waste water sludge, bagasse, and Jerusalem artichoke.

The actual values for the various substrates were obtained as follows:

| Bagasse | | |
|---|---|---|
| Mesophilic (30° C.): | | |
| mass of treated biomass(g): | | 10 |
| dry material content (%) | | 92.03 |
| dry material/experiment (g): | | 9.203 |
| Results | control | *E. cloacae*: |
| Total gas volume at 30° per 1 g dry matter (ml): | 49.2 | 88.0 |
| Degree of intensification (%): | 100 | 178.8 |
| Thermophilic (55° C.): | | |
| mass of treated biomass (g): | | 10 |
| dry material content (%) | | 92.03 |
| dry material/experiment (g): | | 9.203 |
| Results | control | *C. saccharolyticus* |
| Total gas volume at 30° per 1 g dry matter (ml): | 96.2 | 169.2 |
| Degree of intensification (%): | 100 | 175.9 |

| Sweet sorghum (FIGS. 11.a. and 11.b.) | | |
|---|---|---|
| Mesophilic (30° C.): | | |
| mass of treated biomass (g): | | 15 |
| dry material content (%) | | 80 |
| dry material/experiment (g): | | 12 |
| Results | control | *E. cloacae*: |
| Total gas volume at 30° per 1 g dry matter (ml): | 47.9 | 75 |
| Degree of intensification (%): | 100 | 156.5 |
| Thermophilic (55° C.): | | |
| mass of treated biomass (g): | | 15 |
| dry material content (%) | | 68.33 |
| dry material/experiment (g): | | 10.25 |
| Results | control | *C. saccharolyticus* |
| Total gas volume at 30° per 1 g dry matter (ml): | 118.1 | 205.5 |
| Degree of intensification (%): | 100 | 174.0 |

| Jerusalem artichoke, green biomass | | |
|---|---|---|
| Mesophilic (30° C.): | | |
| mass of treated biomass (g): | | 10 |
| dry material content (%) | | 94.6 |
| dry material/experiment (g): | | 9.46 |
| Results | control | *E. cloacae* |
| Total gas volume at 30° per 1 g dry matter (ml): | 42.1 | 70.71 |
| Degree of intensification (%): | 100 | 168.1 |
| Thermophilic (55° C.): | | |
| mass of treated biomass (g): | | 10 |
| dry material content (%) | | 91.9 |
| dry material/experiment (g): | | 9.19 |

| Jerusalem artichoke, green biomass | | |
|---|---|---|
| Results | control | *C. saccharolyticus* |
| Total gas volume at 30° per 1 g dry matter (ml): | 84.8 | 119.5 |
| Degree of intensification (%): | 100% | 140.9 |

| Jerusalem artichoke, tuber | | |
|---|---|---|
| Mesophilic (30° C.): | | |
| mass of treated biomass (g): | | 28 |
| dry material content (%) | | 36.8 |
| dry material/experiment (g): | | 10.3 |
| Results | control | *E. cloacae* |
| Total gas volume at 30° per 1 g dry matter (ml): | 74.0 | 109.0 |
| Degree of intensification (%): | 100 | 147.2 |
| Thermophilic (55° C.): | | |
| mass of treated biomass (g): | | 28 |
| dry material content (%) | | 21.14 |
| dry material/experiment (g): | | 5.9192 |
| Results | control | *C. saccharolyticus* |
| Total gas volume at 30° per 1 g dry matter (ml): | 142.5 | 222.7 |
| Degree of intensification (%): | 100% | 156.1 |

| Waste water sludge | | | | |
|---|---|---|---|---|
| Mesophilic (30° C.): | control | | *E. cloacae*: | |
| mass of treated biomass (g): | 400 | | 400 | |
| dry material content (%) | 6.8 | | 6.7 | |
| dry material/experiment (g): | 27.2 | | 26.8 | |
| Results | control | | *E. cloacae*: | |
| Total gas volume at 30° per 1 g dry matter (ml): | 47.6 | 47.5 | 70.6 | 65.1 |
| Average: | 47.55 | | 67.85 | |
| Degree of intensification (%): | 100 | | 143 | |
| Thermophilic (55° C.): | control | | *C. saccharolyticus* | |
| mass of treated biomass (g): | 400 | | 400 | |
| dry material content (%) | 4.1 | | 4.1 | |
| dry material/experiment (g): | 16.4 | | 16.4 | |
| Results | control | | *C. saccharolyticus* | |
| Total gas volume at 30° per 1 g dry matter (ml): | 68.4 | 65.7 | 104.6 | 114.6 |
| Average: | 67.05 | | 109.6 | |
| Degree of intensification (%): | 100 | | 163.5 | |

In Table I below the results of this experiment are summarized. One can easily recognize that under thermophilic conditions and upon adding the hydrogen producing bacterium biogas production has been largely intensified in all cases investigated.

TABLE I

Summary table of the results

| Substrate | Hőmérséklet (° C.) | Note | total gas volume at 30° per 1 g dry matter (ml) |
|---|---|---|---|
| Bagasse | 30 | Control | 49 |
| Bagasse | 30 | Entero | 88 |
| Bagasse | 55 | Control | 96 |
| Bagasse | 55 | Caldi | 169 |
| Sweet sorghum | 30 | Control | 48 |
| Sweet sorghum | 30 | Entero | 75 |
| Sweet sorghum | 55 | Control | 118 |
| Sweet sorghum | 55 | Caldi | 205 |
| Jerusalem artichoke, tuber | 30 | Control | 74 |
| Jerusalem artichoke, tuber | 30 | Entero | 109 |
| Jerusalem artichoke, tuber | 55 | Control | 143 |
| Jerusalem artichoke, tuber | 55 | Caldi | 223 |
| Jerusalem artichoke, green biomass | 30 | Control | 42 |
| Jerusalem artichoke, green biomass | 30 | Entero | 71 |
| Jerusalem artichoke, green biomass | 55 | Control | 85 |
| Jerusalem artichoke, green biomass | 55 | Caldi | 119 |
| Waste water sludge | 30 | Control | 47 |
| Waste water sludge | 30 | Entero | 68 |
| Waste water sludge | 55 | Control | 67 |
| Waste water sludge | 55 | Caldi | 110 |

Example 8

Field Experiment in a Small Scale Fermentor

The beneficial effect of the addition of a thermophilic anaerobic, hydrogen producer has been demonstrated in a filed experiment. The fermenter was erected on a pig farm that has approximately 12000 pigs. The main unit of the set-up is the fermenter, which is a single reactor space, anaerobic fermenter having a total volume of 15 m$^3$. The operational temperature was 55° C., this was maintained with the help of a built in heating coil in which hot water was circulated. The completely stirred fermenter was filled up with 6 m$^3$ of pig slurry.

In this and previous experiments the anaerobic degradation was initiated by adding a small and constant volume of spent waste water sludge, the effluent of the anaerobic fermenter operating at the "Bacsviz" Regional and Household waste water treatment facility of the city of Kecskemet (6000 Mindszenti krt. 36 Kecskemét, Hungary). It should be noted that biogas production starts without the addition of the spent sludge, but later.

The fermenter works in a semi-continuous mode of operation, every day 10% of the fermenter volume is replaced with fresh substrate. A gas storage container hold the biogas and prevents potentially dangerous backflow of the gas and/or substrate. The biogas then passes through a water vapor removing device (cold finger) before it passes through a gas volume metering device that records the biogas production in a continuous manner. Gas samples are collected at this point in order to follow the changes in gas composition. A gas torch then burns the biogas for safety reasons, in order to avoid risk of explosion.

The fermenter is air tight and thus establishes and maintains anaerobic conditions. The biogas generated at the beginning of the process replaces air above the liquid phase in the fermenter. Alternatively, anaerobicity can be established by purging the fermenter with nitrogen or carbon dioxide gases. At the start-up of the operation the fermenter was almost completely filled with pig slurry, the volume of which was continuously lowered to a level of 6 m$^3$.

Figure 12:
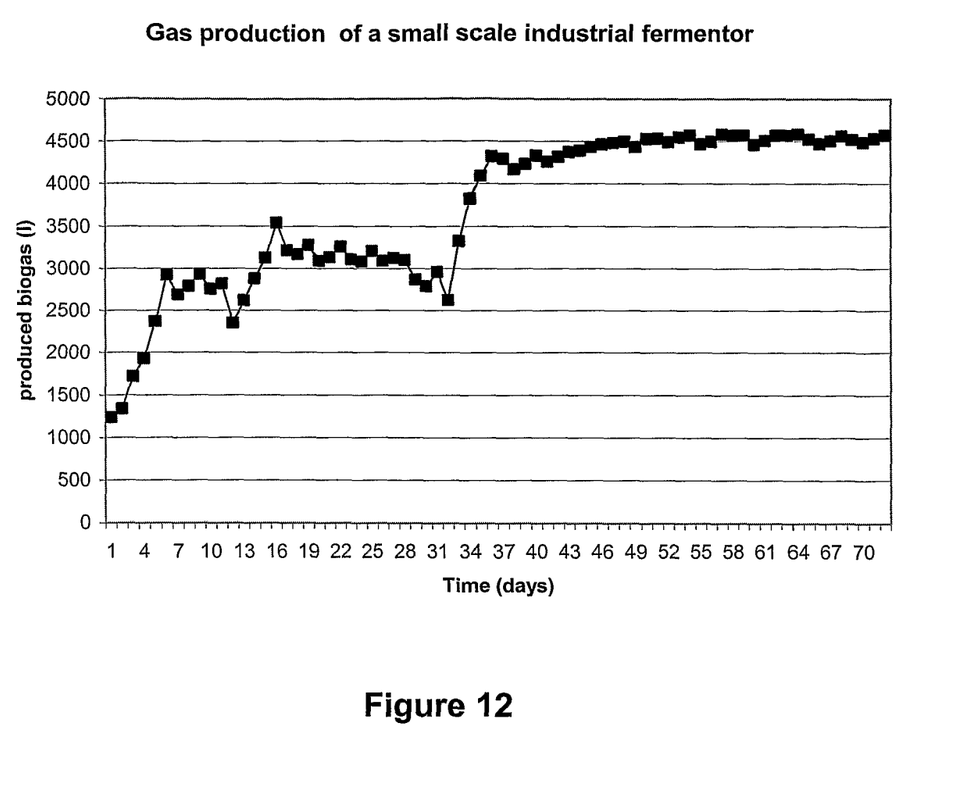
FIG. 12 demonstrates the biogas production in a 15 m$^3$ thermophilic industrial fermenter. The fermenter contained 6 m$^3$ of pig slurry as substrate. The system was operated in a semi continuous feeding mode.

During the initial period the control or basal biogas production was recorded until stable operation was established. The anaerobic treatment was started on Sep. 10, 2005, the gas production became stable after 6 days indicating that the start-up strategy was very well performed. A few days is a usual time-period for reaching an approximately constant level of gas production in fermenters. After stable operation was reached, the performance of the fermenter was recorded for an additional 31 days to make sure that the "baseline" spontaneous biogas production could be maintained at the same level. On day 31 the fermenter was inoculated with a precultivated culture of *Caldicellulosiruptor saccharolyticus* at a volumetric concentration of 10 V/V %. An equal volume of substrate was removed from the fermentor before inoculation so that the same fermented volume remained in the fermenter. FIG. 12 shows that biogas production increased significantly after the inoculation and has been stable at this elevated level for at least two months (at least till Nov. 26, 2005). The experiment is still going on in order to determine the length of the intensification in time after the inoculation.

Some of the essential features and beneficial effects of the biotechnological biogas intensification technology of the invention are summarized below.

The invention brings about modifications in the anaerobic biomass treatment technologies, which increases the efficacy of already existing biogas plants and shortens the pay-out period of newly established ones by implementing a relatively simple process. In the solution the newly recognized advantageous properties of the participating microorganisms are exploited.

The technology converts organic waste and byproducts of agriculture and the food production industry and communal organic waste in a closed process into biogas and biofertilizer. As a result, the environmentally dangerous organic biomass, which is frequently considered as "waste" is recycled without the production of other pollutants. The products of the improved anaerobic treatment technology are useful for renewable energy carrier and as a fertilizer.

The technology can be adopted to every known and currently used anaerobic biological treatment processes. It is particularly beneficial in animal farms dealing with at least 200 animals having a unit size of 500 kg each or equivalent smaller livestock. The technology gives excellent results with animal manure or sludge, solid, mixed or liquid other organic wastes, communal solid wastes, waste water sludge, and various agricultural and food industrial wastes.

The advantages of using the novel technology as described in the present application offers the following benefits for anaerobic treatment processes.

1. The biogas that is formed in excess quantities is a valuable renewable energy carrier. It can be used in heating as well as in electricity generation.
2. The effluent of the fermenter is an excellent natural fertilizer that is much better than direct application of animal manure because:
   the valuable nitrogen content is preserved during anaerobic fermentation;
   the acidity of the material decreases, its pH normally increases from pH=7 to pH=8.
   the C/N ratio decreases by 30-50%, which makes the effluent suitable for direct application on agricultural crops;

the important phosphorus and potassium content is converted into forms that are easily adsorbed by plants;

the seeds of weeds are damaged during the anaerobic treatment, therefore a lowered amount of viable weed seeds is found in the effluent;

the product represent significantly less odor nuisance and can be dewatered easier than fresh manure.

3. The effluent of an anaerobic fermenter decreases the public health problems associated with waste disposal because:

the major part of the human pathogens are killed during anaerobic treatment;

the volume of the biomass decreases therefore the effluent is easier to deposit;

the concentration of the environmentally hazardous components decreases, e.g., the BOI is lower by 60-70% and the COI decreases by 50-60% after anaerobic fermentation;

4. The technology as described herein facilitates the economically feasible and technologically stable operation of the simple single reactor systems. The initial investment costs remain at low level, which makes the biogas producing technology financially affordable for smaller entities as well.

The invention claimed is:

1. A method for increasing methane production in a biomass fermenting system, in which biomass is fermented under anaerobic and thermophilic conditions by a consortium comprising polymer degrading microorganisms, acetogenic microorganisms and methanogenic microorganisms, wherein methane production is increased by adding a thermophilic, anaerobic, acetogenic, hydrogen-producing bacterium selected from the group consisting of *Thermotoga, Thermococcus, Pyrococcus, Clostridium, Ruminococcus* and *Caldicellulosiruptor* genus.

2. The method of claim 1, wherein before the start of biogas production or during biogas production, a culture of thermophilic, anaerobic, acetogenic, hydrogen-producing microorganism is added, one or more times, to the biogas producing consortium.

3. The method of claim 1, wherein the thermophilic, anaerobic, acetogenic, hydrogen producing bacterium is *Caldicellulosiruptor saccharolyticus*.

4. The method of claim 1, wherein a pure culture of *Caldicellulosiruptor saccharolyticus* is used.

5. The method of claim 1, wherein the biomass is
liquid manure,
waste water sludge or
plant waste, or any mixture thereof.

6. The method of claim 1, further comprising before or during fermentation adding to the biomass a material utilizable as a nutrient by any of the microorganisms and/or a material of increased surface area.

7. The method of claim 1, wherein the bacterium culture is applied, relative to the volume of the biomass, in a ratio of 5 to 20 v/v %.

8. The method of claim 1, wherein the biomass is fermented in a fermentor having a single reactor vessel or a single reactor space.

9. The method of claim 1, wherein said thermophilic, anaerobic, acetogenic, hydrogen-producing bacterium has a polymer degrading activity, wherein said polymer is a carbohydrate.

10. The method of claim 1, comprising the steps of:

starting the fermentation of the biomass by setting its temperature to 45-70° C., or to 50-60° C.

inoculating the biomass with an inoculum comprising polymer-degrading microorganisms, acetogenic microorganisms and/or methanogenic microorganisms;

providing anaerobic conditions for fermentation;

before the start of the fermentation or during fermentation, inoculating the biogas producing system with a culture of thermophilic, anaerobic, acetogenic, hydrogen-producing bacterium;

carrying on the fermentation at 45-70° C. under anaerobic conditions; and collecting or utilizing the produced methane-containing biogas.

11. The method of claim 5, wherein plant waste is from high energy plants.

12. The method of claim 6, wherein the cells of the hydrogen producing bacterium are sedimented or are bound to a high specific surface, inert carrier.

13. The method of claim 7, wherein the ratio is 10 v/v %.

14. The method of claim 1, wherein the biomass is fermented in a continuous operation system, wherein:

the produced biogas and or the produced fermented biomass is removed continuously or at multiple given periods of time; and the thermophilic, anaerobic, acetogenic, hydrogen producing bacterium is fed to the fermentor continuously or at multiple given periods of time.

15. The method of claim 10, wherein the fermentation is started and carried on at 50° C.-60° C.

16. The method of claim 12, wherein the inert carrier is perlite.

* * * * *